(12) United States Patent
Melozzi

(10) Patent No.: US 10,507,114 B2
(45) Date of Patent: Dec. 17, 2019

(54) UNIVERSAL PROSTHETIC HEAD FOR HIP PROSTHESIS

(71) Applicant: Alessandro Melozzi, Teramo (IT)

(72) Inventor: Alessandro Melozzi, Teramo (IT)

( * ) Notice: Subject to any disclaimer, the term of this patent is extended or adjusted under 35 U.S.C. 154(b) by 13 days.

(21) Appl. No.: 15/587,623

(22) Filed: May 5, 2017

(65) Prior Publication Data

US 2017/0319347 A1 Nov. 9, 2017

(30) Foreign Application Priority Data

May 9, 2016 (IT) .................. 102016000047392

(51) Int. Cl.
| | |
|---|---|
| *A61F 2/32* | (2006.01) |
| *A61F 2/34* | (2006.01) |
| *A61F 2/36* | (2006.01) |
| *A61F 2/30* | (2006.01) |

(52) U.S. Cl.
CPC ........ *A61F 2/3609* (2013.01); *A61F 2/30771* (2013.01); *A61F 2/32* (2013.01); *A61F 2/34* (2013.01); *A61F 2002/3082* (2013.01); *A61F 2002/30332* (2013.01); *A61F 2002/30604* (2013.01); *A61F 2002/30607* (2013.01); *A61F 2002/30642* (2013.01); *A61F 2002/30774* (2013.01); *A61F 2002/30934* (2013.01); *A61F 2002/3208* (2013.01); *A61F 2002/3401* (2013.01); *A61F 2002/3424* (2013.01); *A61F 2002/3443* (2013.01); *A61F 2002/3458* (2013.01); *A61F 2002/3615* (2013.01); *A61F 2310/00023* (2013.01); *A61F 2310/00029* (2013.01); *A61F 2310/00131* (2013.01); *A61F 2310/00407* (2013.01); *A61F 2310/00796* (2013.01)

(58) Field of Classification Search
CPC combination set(s) only.
See application file for complete search history.

(56) References Cited

U.S. PATENT DOCUMENTS

| | | | |
|---|---|---|---|
| 5,919,236 A | 7/1999 | Pfaff et al. | |
| 9,700,418 B2 * | 7/2017 | Melozzi | ............... A61F 2/32 |
| 2005/0149199 A1 * | 7/2005 | Steinberg | ........... A61F 2/30742 |
| | | | 623/22.23 |

(Continued)

FOREIGN PATENT DOCUMENTS

| | | |
|---|---|---|
| EP | 2843294 A1 | 3/2015 |
| WO | 2011006852 A1 | 1/2011 |

*Primary Examiner* — Bruce E Snow
(74) *Attorney, Agent, or Firm* — Egbert, McDaniel & Swartz, PLLC

(57) ABSTRACT

A prosthetic head with a body having the shape of a cup shaped as a hemispherical cap provided with an external surface, an internal surface and a lower edge shaped as a circumference, fixing means to fix the prosthetic head to the cotyle, and a projection abutting from the internal surface of the prosthetic head in such manner to define an annular step, and a truncated-conical portion obtained in the internal surface of the body of the prosthetic head starting from the lower edge of the prosthetic head, the truncated-conical portion of the prosthetic head being suitable for being coupled in conical coupling mode with a truncated conical part of an insert intended to be inserted in the prosthetic head. he projection is shaped as a portion of a spherical cap.

10 Claims, 12 Drawing Sheets

(56) References Cited

U.S. PATENT DOCUMENTS

| | | | | |
|---|---|---|---|---|
| 2006/0229731 A1* | 10/2006 | Newsome | .................. | A61F 2/34 |
| | | | | 623/22.19 |
| 2010/0131073 A1* | 5/2010 | Meridew | .................... | A61F 2/34 |
| | | | | 623/22.28 |
| 2011/0054628 A1* | 3/2011 | Banks | ........................ | A61F 2/32 |
| | | | | 623/22.19 |
| 2017/0290666 A1* | 10/2017 | Behzadi | .................... | A61F 2/34 |

\* cited by examiner

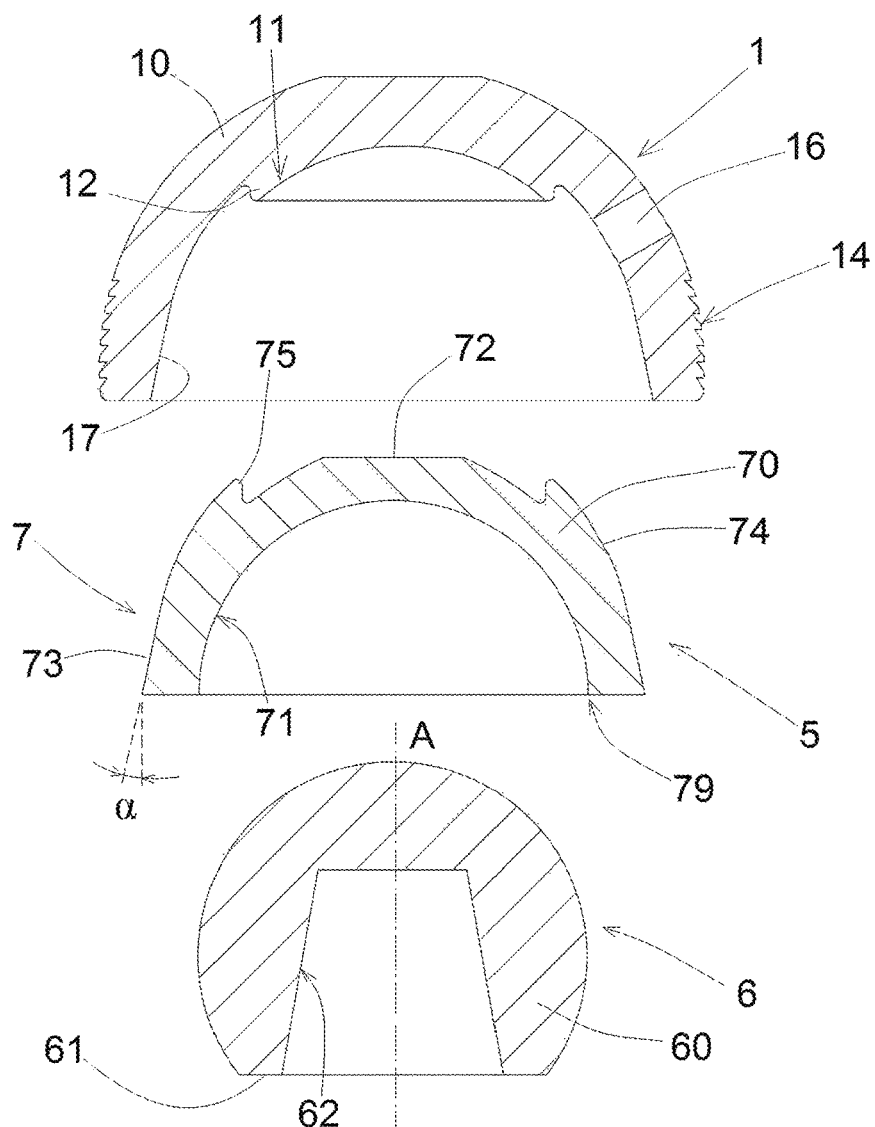
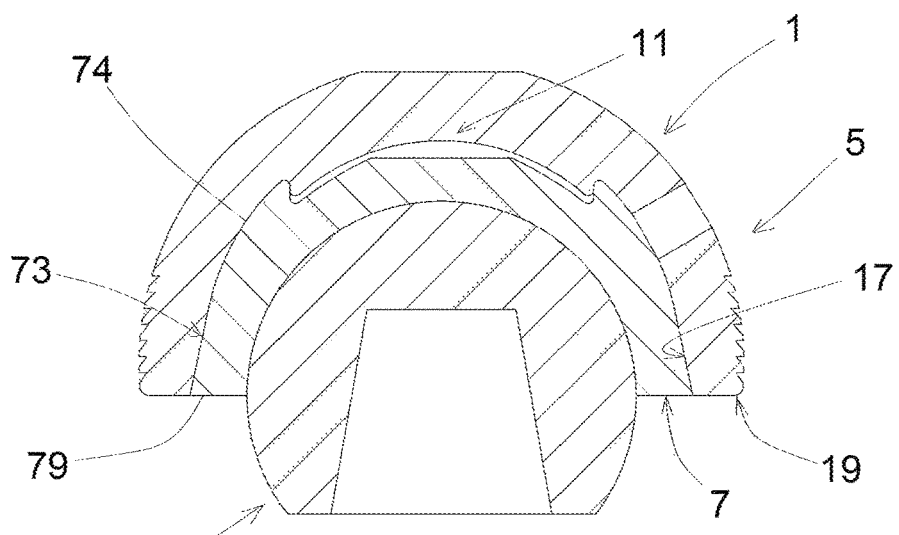
FIG. 5
FIG. 6

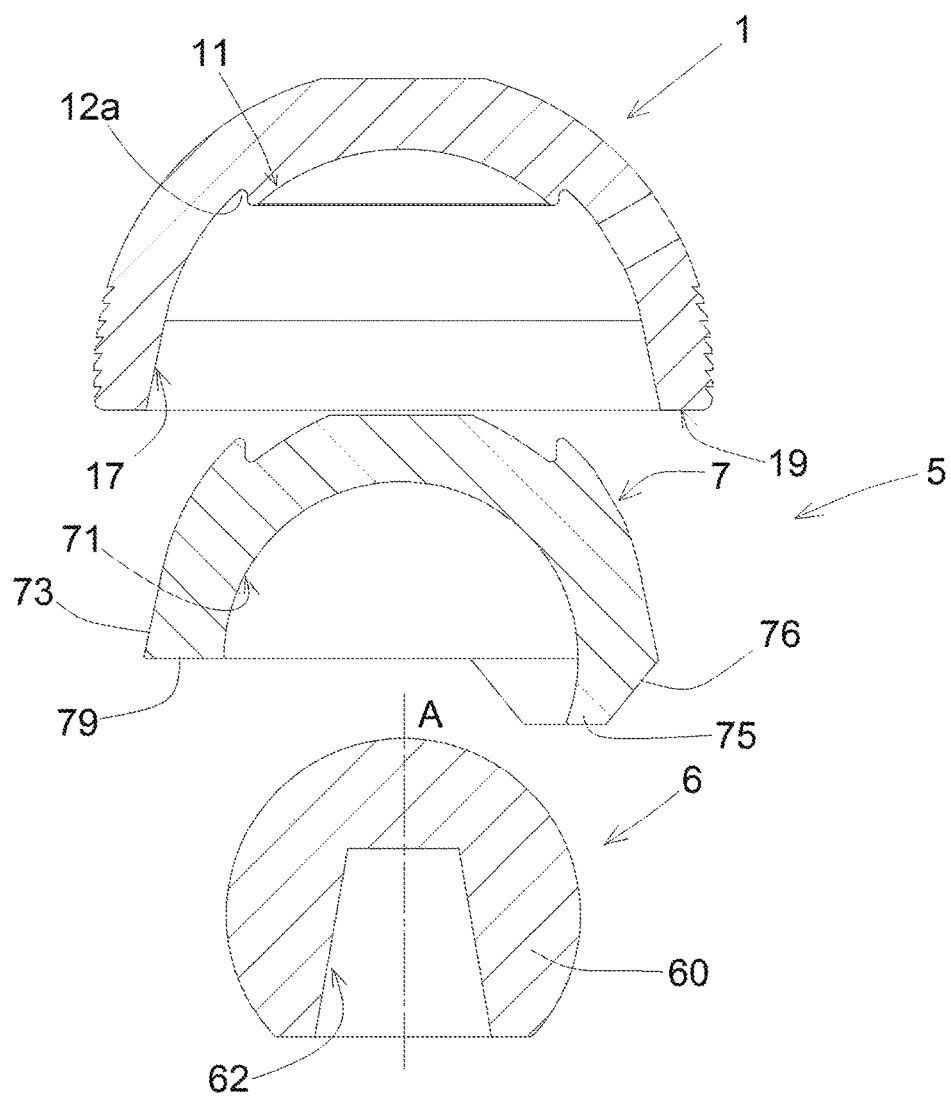
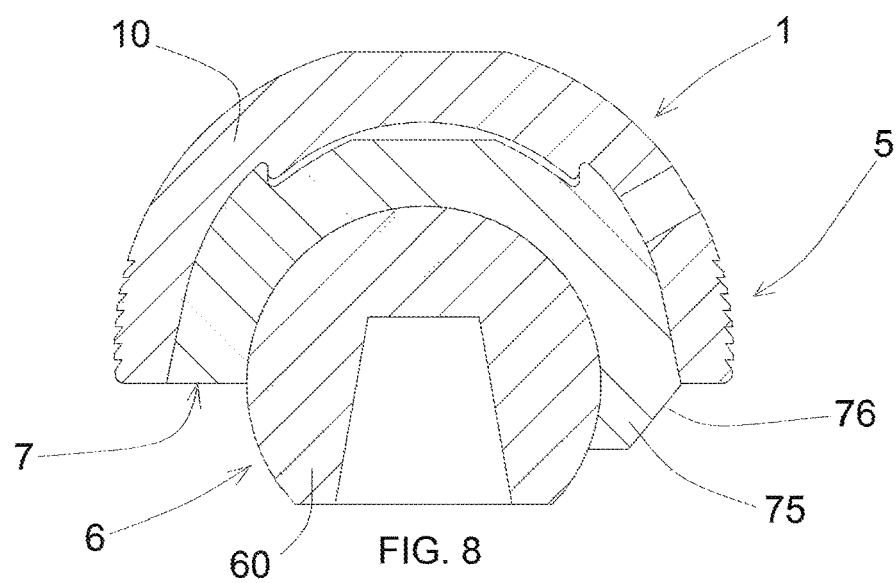

UNIVERSAL PROSTHETIC HEAD FOR HIP PROSTHESIS

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present patent application for industrial invention relates to a universal prosthetic head suitable for being applied to two different types of hip prosthesis, that is to say to a conventional hip prosthesis and to an inverse hip prosthesis.

2. Description of Related Art Including Information Disclosed Under 37 CFR 1.97 and 37 CFR 1.98

Conventional hip prostheses are known, wherein the prosthesis attempts to reproduce the normal hip joint. In such a case, the conventional prosthesis comprises:
  a stem intended to be fixed to a femur;
  a ball fixed to the stem in order to reproduce the head of the femur; and
  a cup intended to be fixed to a cotyle or acetabulum.

In this way, the ball joined to the femur can move in spherical coupling mode with respect to the cup joined to the cotyle.

One or two cup-shaped inserts may be disposed between the ball and the cup in order to facilitate the movement of the ball with respect to the cup.

Inverse hip prostheses are known, wherein the positions of the ball and of the cup are inverted with respect to the anatomical prostheses. In such a case, the ball is joined to or placed on a prosthetic head intended to be fixed to the cotyle, whereas the cup is joined to the stem that is intended to be fixed to the femur.

Inverse hip prostheses are recommended for patients affected by specific pathologies; in fact, the muscles used for the movement of the inverse prosthesis are different from the ones used for the movement of the conventional prosthesis.

WO2011/006852, in the name of the same applicant, describes an inverse prosthesis having a prosthetic head with an internally projecting portion that is stopped against the ball in such a way to generate an air space between ball and prosthetic head, wherein the cup joined to the stem is inserted.

Obviously, the prosthetic head of such an inverse prosthesis cannot be adapted to a conventional prosthesis.

FR2843294 describes a conventional hip prosthesis comprising a prosthetic head intended to be fixed to a cotyle and a hemispherical body disposed inside the prosthetic head and having an external surface with a truncated-conical portion intended to be coupled in conical coupling mode with a truncated-conical portion of the prosthetic head. A hemispherical core is disposed inside the hemispherical body to house a ball fixed to a stem intended to be fixed to a femur.

U.S. Pat. No. 5,919,236 discloses a conventional hip prosthesis comprising a metal prosthetic head intended to be fixed to a cotyle, and a hemispherical insert having an internal surface suitable for being coupled in spherical coupling mode with a ball, and an external surface with a truncated-conical portion suitable for being coupled in conical coupling mode with a truncated-conical portion of the prosthetic head.

BRIEF SUMMARY OF THE INVENTION

The purpose of the present invention is to eliminate the drawbacks of the prior art by disclosing a prosthetic head intended to be used both for an inverse prosthesis and a conventional prosthesis.

This purpose is achieved according to the invention with the characteristics of the independent claim 1.

Advantageous embodiments of the invention appear from the dependent claims.

The prosthetic head according to the invention is suitable for inverse hip prostheses and conventional hip prostheses. Such a prosthetic head is intended to be fixed to a cotyle. The prosthetic head comprises:
  a body having the shape of a cup substantially shaped as a hemispherical cap, provided with an external surface, an internal surface and a lower edge shaped as a circumference;
  fixing means to fix the prosthetic head to the cotyle;
  a projection abutting from the internal surface of the prosthetic head in such manner to define an annular step, and a truncated-conical portion obtained in the internal surface of the body of the prosthetic head starting from said lower edge of the prosthetic head. Such truncated-conical portion of the prosthetic head is suitable for being coupled in conical coupling mode with a truncated-conical portion of an insert intended to be inserted in the prosthetic head.

The peculiar characteristic of said prosthetic head is represented by the fact that the projection abutting from the internal surface of the prosthetic head is shaped as a portion of spherical cap.

BRIEF DESCRIPTION OF THE SEVERAL VIEWS OF THE DRAWINGS

Additional features of the invention will appear clear from the detailed description below, which refers to merely illustrative, not limiting embodiments, wherein:
FIG. 5 is an exploded axial view of a conventional prosthesis with the prosthetic head of FIG. 2;

FIG. 6 is an axial view of the conventional prosthesis of FIG. 5 in assembled condition;

FIG. 7 is an exploded axial view of a variant of the conventional prosthesis of FIG. 5;

FIG. 8 is an axial view of the conventional prosthesis of FIG. 7 in assembled condition;

DETAILED DESCRIPTION OF THE INVENTION

Figure 1:
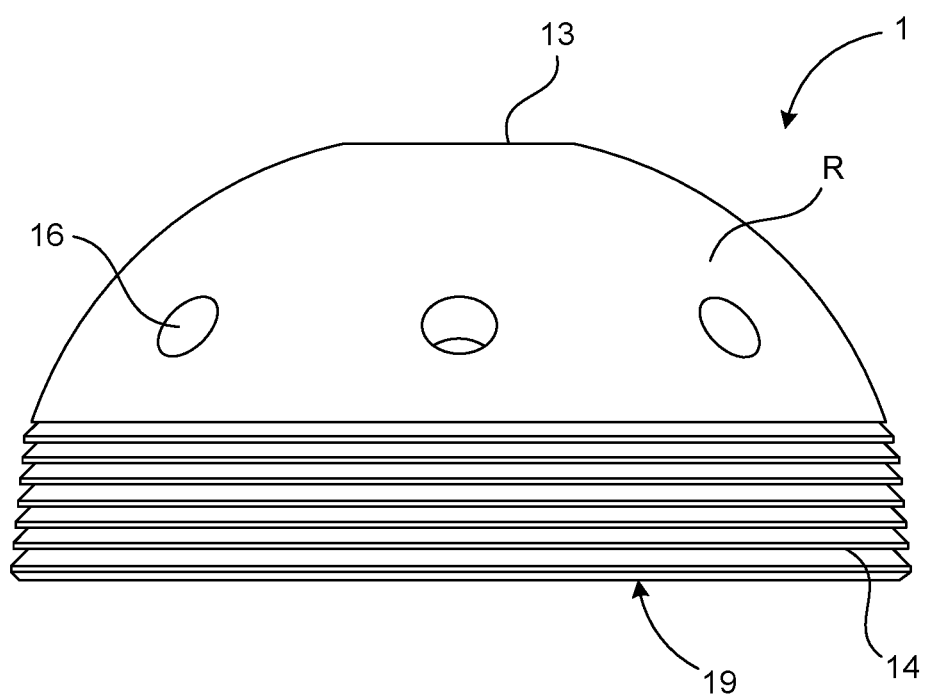
FIG. 1 is a view of a prosthetic head according to the invention.
Figure 2:
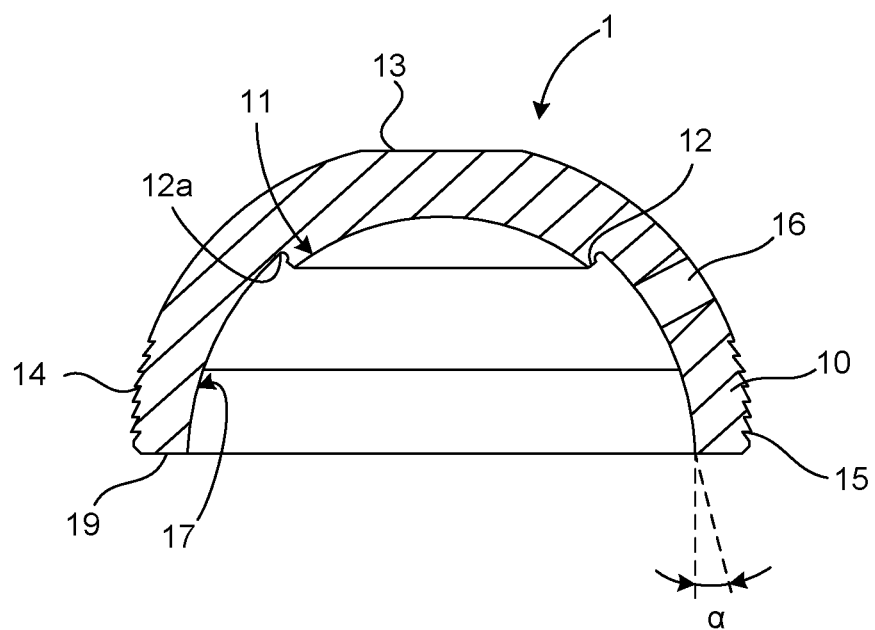
FIG. 2 is an axial view of the prosthetic head of FIG. 1.

With reference to FIGS. 1 and 2 a prosthetic head according to the invention is described, which is generally indicated with reference numeral 1.

The prosthetic head (1) comprises a body (10) having the shape of a cup substantially shaped as a hemispherical cap, and having suitable dimensions in order to be fixed to a cotyle.

The body (10) of the prosthetic head has a flattened pole (13) and a lower edge (19) shaped as a circumference.

A projection (11) abuts towards the interior of the prosthetic head, in such manner to form an annular step (12). The projection (11) is shaped as a portion of spherical cap subtended by a central angle of approximately 60-90°.

Advantageously, the annular step (12) has a saw-toothed or "V"-shaped crosssection, in such manner to define a seat (12a) between the annular step (12) and the internal surface of the prosthetic head.

Through holes (16) are obtained in the body (10) of the prosthetic head to receive fixing screws for fixing the prosthetic head to the cotyle.

The prosthetic head (1) also comprises grooves (15) obtained in the external surface of the prosthetic head, in such a way to define ribs (14). The grooves (15) provide a primary anchoring of the prosthetic head (4) to the cotyle. For this purpose, the cotyle is prepared with suitable cutters that are under-dimensioned by one size with respect to the prosthetic head. Therefore, a primary stability of the prosthesis is obtained upon installation with a pressfit coupling between prosthetic head and cotyle. Such primary stability is improved with fixing screws that are engaged in the holes (16) of the prosthetic head and are screwed in the cotyle.

The grooves (15) are disposed in a lower portion of the prosthetic head, that is to say in an equatorial area of the prosthetic head with higher diameter, that is to say in a peripheral part of the prosthetic head. The grooves (15) are circumferential grooves obtained by means of notches on the external surface of the prosthetic head, starting from the lower edge (19) of the prosthetic head.

In this way, each circumferential groove (15) is defined between two circumferential ribs (14). Cross-sectionally, the circumferential ribs (14) and the circumferential grooves (15) have a substantially arched or sinuosoid or saw-toothed shape.

The grooves (15) are obtained in the peripheral part of the prosthetic head and extend from the lower edge (19) of the prosthetic head to a latitude of approximately 20°-30°. For illustrative purpose, six circumferential ribs (14) and seven circumferential grooves (15) are provided.

The grooves (15) are circular concentric circumferential grooves, and define circumferential ribs (14) with a tapered shape, with increasing dimensions going towards the lower edge of the prosthetic head. The circumferential ribs (14) have a triangular saw-toothed section. In this way the press-fit coupling between the prosthetic head and the cotyle is made easier, avoiding a possible pull-out, or separation, or displacement of the prosthetic head from the cotyle.

Alternatively, the grooves (15) may be defined by a helical thread wound around the external surface of the prosthetic head. Such a thread is of selftapping type. In this way the prosthetic head (1) is screwed into the cotyle and a possible pull-out, or separation, or displacement of the prosthetic head from the cotyle is avoided.

The prosthetic head (4) has a rough surface (R) that extends on the entire external surface of the prosthetic head, except for the grooves (15) and the ribs (14). The rough surface (R) permits a growth of the regenerated bone and is therefore used to guarantee a secondary stability of the prosthesis when the regenerated bone gradually grows on the rough surface (R) of the prosthetic head.

The rough surface (R) can be obtained with the same material as the prosthetic head (1) or with a coating material of the prosthetic head. For illustrative purposes, the prosthetic head (1) is made of chrome-cobalt alloy, titanium alloy or electrowelded trabecular titanium or tantalum.

If the prosthetic head is made of trabecular titanium, the rough surface (R) is obtained with titanium powder electrowelding and with a hydroxyapatite coating on the trabecular titanium.

On the contrary, if the prosthetic head is made of chrome-cobalt alloy, the rough surface (R) is obtained with chrome-cobalt powder electrowelding and with a hydroxyapatite coating on the electrowelded chrome-cobalt powder.

Instead, if the prosthetic head is made of nitrogen-enriched steel, the rough surface (R) has a porous titanium powder coating and a hydroxyapatite coating.

Hydroxyapatite is a rare mineral with $Ca_5(PO_4)_3(OH)$ chemical composition. Hydroxyapatite can be used as filler to replace amputated bones, or as coating to stimulate the bone growth inside prosthetic implants.

The body (10) of the prosthetic head has an internal surface with a truncated-conical portion (17). The truncated-conical portion (17) is obtained in the peripheral part of the prosthetic head and extends from the lower edge (19) of the prosthetic head to a latitude of approximately 20°-30°. Otherwise said, the truncated-conical portion (17) is opposed to the grooves and ribs (15,14) obtained on the external surface of the prosthetic head.

The truncated-conical portion (17) has a coning angle ($\alpha$) comprised between 10 and 30°. The coning angle ($\alpha$) is calculated with respect to a straight line that is parallel to an axis of the prosthetic head orthogonal to the plane passing through the lower edge (19) of the prosthetic head.

In the following description the parts that are identical or correspond to the parts described above are identified with the same numerals, omitting their detailed description.

Figure 3:
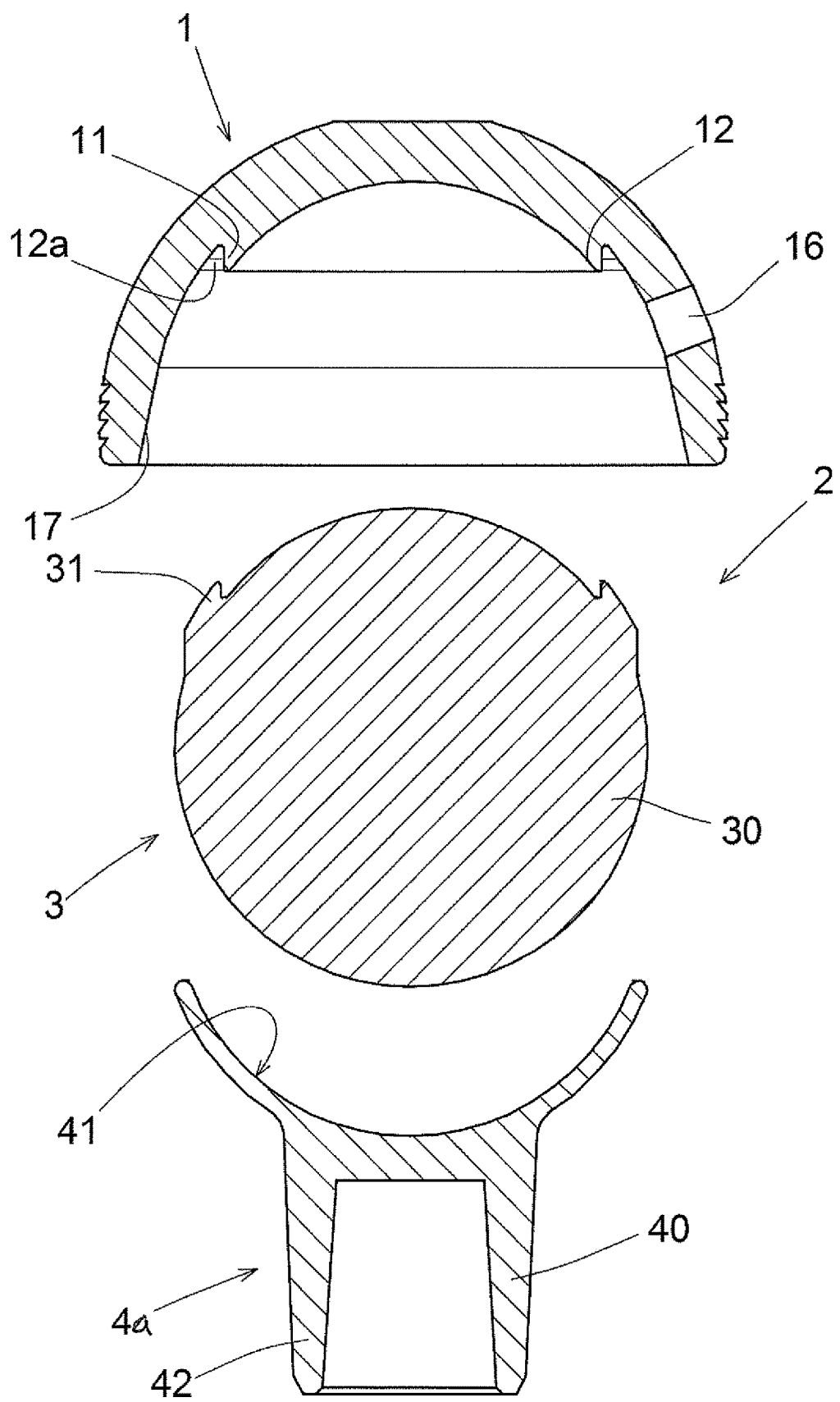
FIG. 3 is an exploded axial view of an inverse prosthesis with the prosthetic head of FIG. 2.
Figure 4:
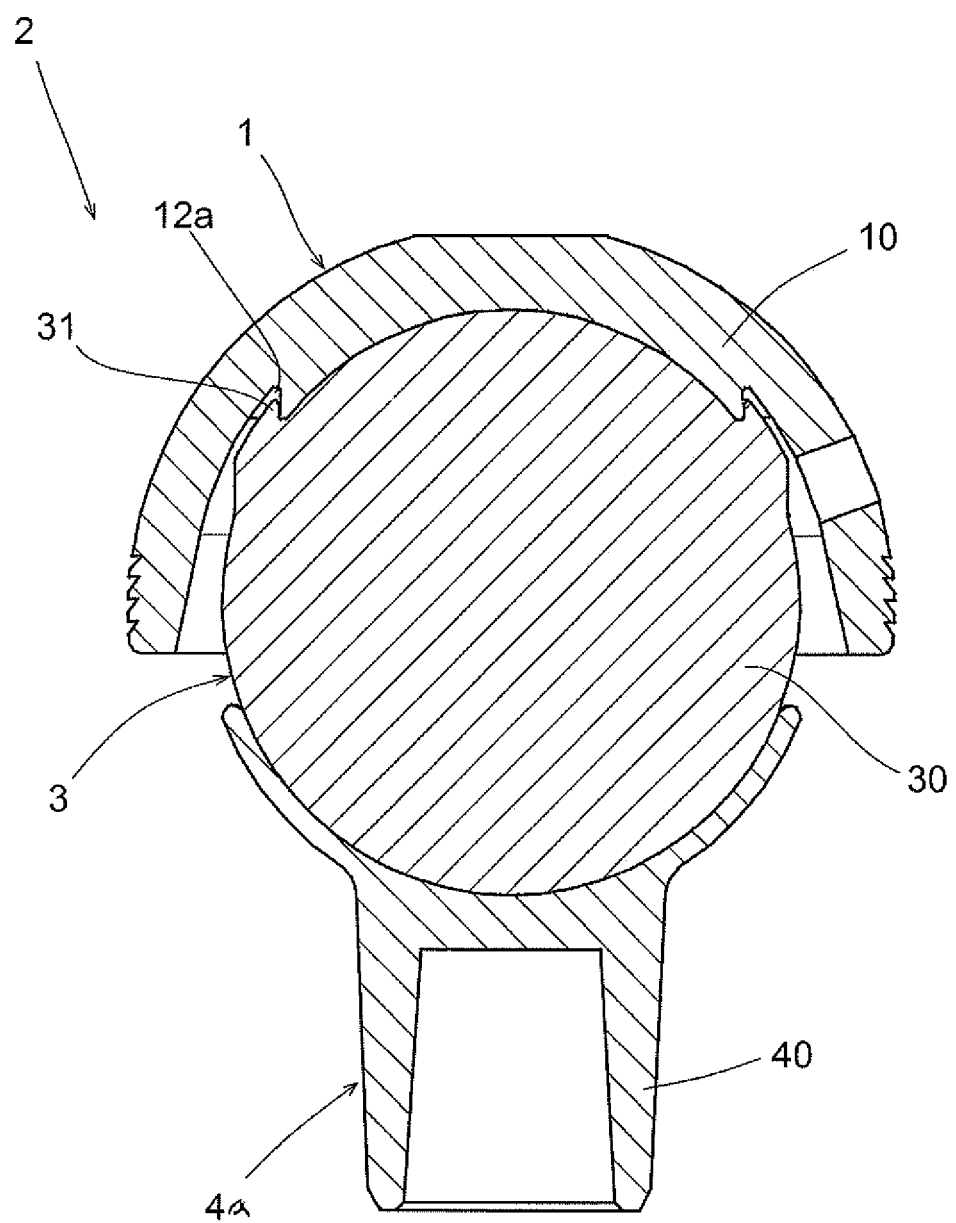
FIG. 4 is an axial view of the inverse prosthesis of FIG. 3 in assembled condition.

With reference to FIGS. 3 and 4, a first embodiment of an inverse prosthesis (2) using the prosthetic head (1) is described.

The inverse prosthesis (2) comprises a ball (3) intended to be placed on the prosthetic head (1) and a distal cup (4*a*) intended to be fixed to a stem that is in turn intended to be fixed to a femur.

The distal cup (4*a*) has a body (40) shaped as a portion of spherical cap, having an internal surface (41) with section shaped as an arc of circle, with a central angle slightly lower than 180°, preferably of approximately 160°.

A shank (42) abuts externally from the distal cup (4), being intended to be engaged in a stem to be fixed to the femur. The shank (42) is internally empty and comprises a cavity intended to receive an upper end of the stem.

Alternatively, the shank (42) can be without cavity and intended to be inserted by pressure in a housing obtained on the upper end of the stem.

The ball (3) has a spherical body (30) intended to be received in the distal cup (4) in spherical coupling mode. An annular collar (31) abuts externally from the spherical body (30). The collar (31) has substantially the same thickness as the step (12) of the projection (11) of the prosthetic head and defines a perimeter that is slightly higher than the perimeter of the step (12) of the projection of the prosthetic head.

In view of the above, the projection (11) of the prosthetic head is disposed inside the collar (31) and is stopped against the body (30) of the ball. The step (12) of the projection of the prosthetic head is stopped against the collar (31). In this way, an air space (I) is formed between the body (30) of the ball and the internal surface of the prosthetic head (1), wherein the body (40) of the distal cup (4) can be inserted. It must be considered that the movement between the prosthetic head (1) and the ball (3) is constrained by the collar (31) of the ball and by the projection (11) of the prosthetic head. Otherwise said, the ball (3) can only rotate with respect to the prosthetic head (1) around the axis passing through the pole of the prosthetic head.

Advantageously, the collar (31) of the ball has a sawtoothed crosssection and the step (12) of the prosthetic head defines a seat (12*a*) that corresponds to the collar (31) of the ball, in such a way to exactly house the collar (31) of the ball. Such a special configuration of the collar (31) of the ball and of the step (12) of the prosthetic head prevents the accidental removal of the ball (3) from the prosthetic head (1), which would result in displacement.

With reference to FIGS. 5 and 6, a first embodiment of a conventional prosthesis (5) using the prosthetic head (1) is described.

The conventional prosthesis (5) comprises a ball (6) intended to be fixed to a stem intended to be fixed to a femur and an insert (7) fixed to the prosthetic head and suitable for receiving the ball (6) in spherical coupling mode.

In such a case, the ball (6) has a spherical body (60) cut along one of its poles in such a way to define a flat lower edge (61). A housing (62) is obtained inside the body of the ball and is open in the lower edge (61) of the ball. The housing (62) is suitable for receiving a stem that is intended to be fixed to the femur. The housing (62) can have a cylindrical or a truncatedconical shape in such manner to generate a conical coupling with the stem. Said housing (62) has an axis (A) that is orthogonal to the lower edge (61) of the spherical body and passes through the center of the spherical body. Alternatively, the axis (A) of the housing (62) may be non-orthogonal to the lower edge (61) of the spherical body and non-passing through the center of the spherical body. By inclining the axis (A) of the housing (62) of the spherical body with respect to the lower edge (61) of the spherical body it is possible to modify the inclination of the stem intended to be fixed to the femur, thus preventing a displacement of the ball (6) joined to the stem fixed to the femur.

Advantageously, the spherical body (60) is made of reticulated polyethylene or polyethylene with vitamin E and a core made of a tubular metal element is disposed in the housing (62). The core has a base surface applied under the lower edge (61) of the spherical body.

The insert (7) has a body (70) shaped as a hemispherical cup with a lower edge (79) with circular shape. The body (70) has an internal surface (71) that is perfectly hemispherical in such a way to receive the ball (6), generating a spherical joint. The insert (7) is made of reticulated polyethylene, polyethylene with vitamin E, or metal.

The body (70) of the insert has an external surface with a flattened pole (72) and a truncated-conical part (73) disposed in peripheral position starting from the lower edge (79). The truncated-conical part (73) of the insert is suitable for being coupled in conical coupling mode with the truncated-conical portion (17) of the prosthetic head.

Otherwise said, the truncated-conical part (73) of the external surface of the insert has a coning angle ($\alpha$) that is substantially equal to the coning angle ($\alpha$) of the truncated-conical part (17) of the prosthetic head. In this way, the insert (7) is firmly fixed to the prosthetic head (1) and cannot move with respect to the prosthetic head (1).

The external surface of the insert has an intermediate part (74) between the truncated-conical part (73) and the pole (72). An annular collar (75) abuts externally from the intermediate part (74) of the external surface of the insert.

As shown in FIG. 6, the conical coupling between the truncated-conical portion (17) of the prosthetic head and the truncated-conical part (73) of the insert is made in such a way that when the insert (7) is coupled with the prosthetic head, the lower edge (19) of the prosthetic head is flush with the lower edge (79) of the insert. In such a case the projection (11) of the prosthetic head is disposed inside the collar (75) of the insert and is stopped against the intermediate part (74) of the external surface of the body of the insert.

Alternatively, the insert (7) can be made of ceramic. In such a case, the intermediate part (74) of the external surface of the insert is shaped as a spherical sector and, when the insert (7) is coupled with the prosthetic head, the projection (11) of the prosthetic head is stopped against the intermediate part (74) of the insert or is disposed at a short distance from it.

Figure 8A:
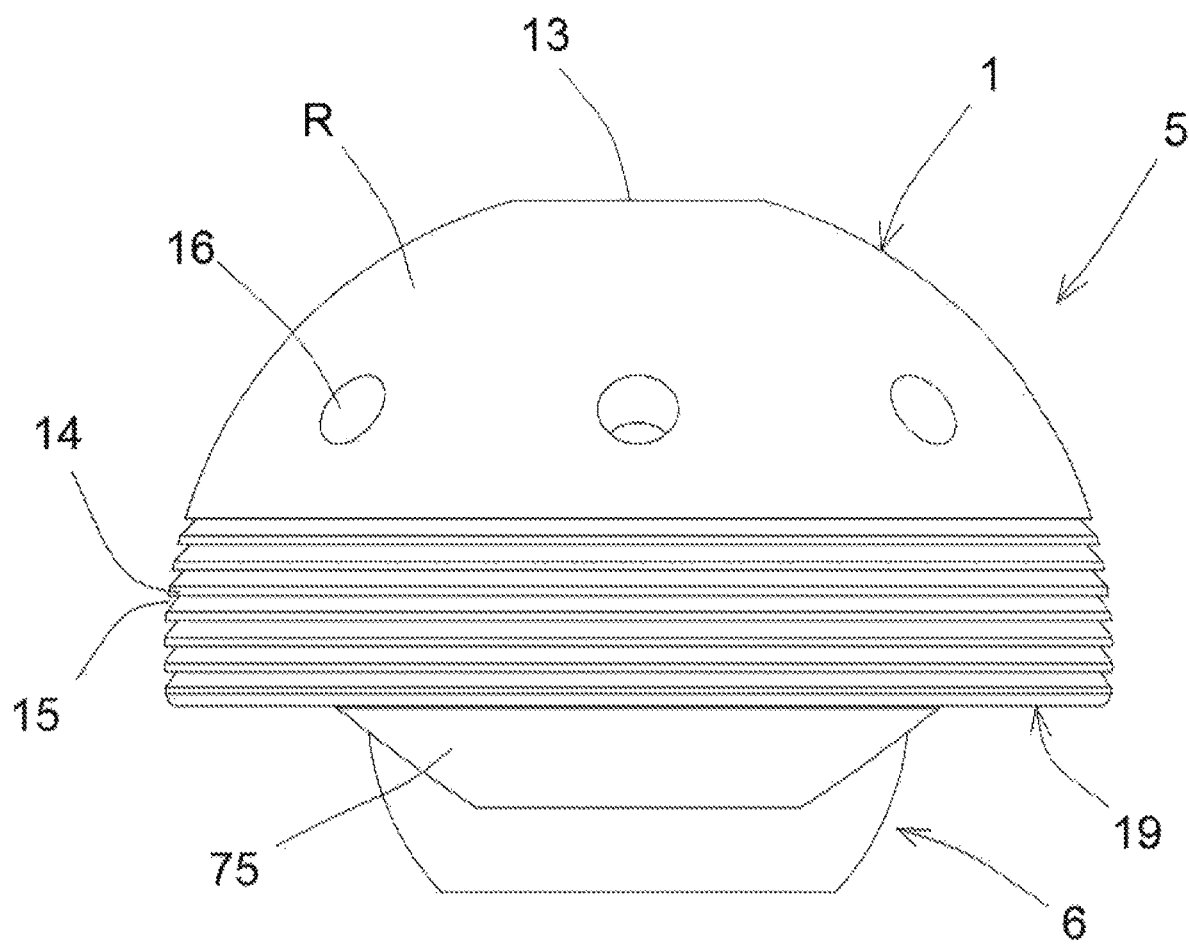
FIG. 8A is a side view of the conventional prosthesis of FIG. 8.

With reference to FIGS. 7, 8 and 8A, a variant of the insert (7) is described. In such a case, the insert (7) comprises a shoulder (75) that projects in lower position with respect to the lower edge (79) of the insert. The shoulder (75) of the insert extends for an angle of approximately 60-90°. The shoulder (75) has a tapered external surface with increasing thickness going from its lower edge upwards. The shoulder (75) of the insert abuts in lower position from the lower edge (19) of the prosthetic head and is used to prevent a displacement of the ball (6) joined to the stem fixed to the femur.

Figure 9:
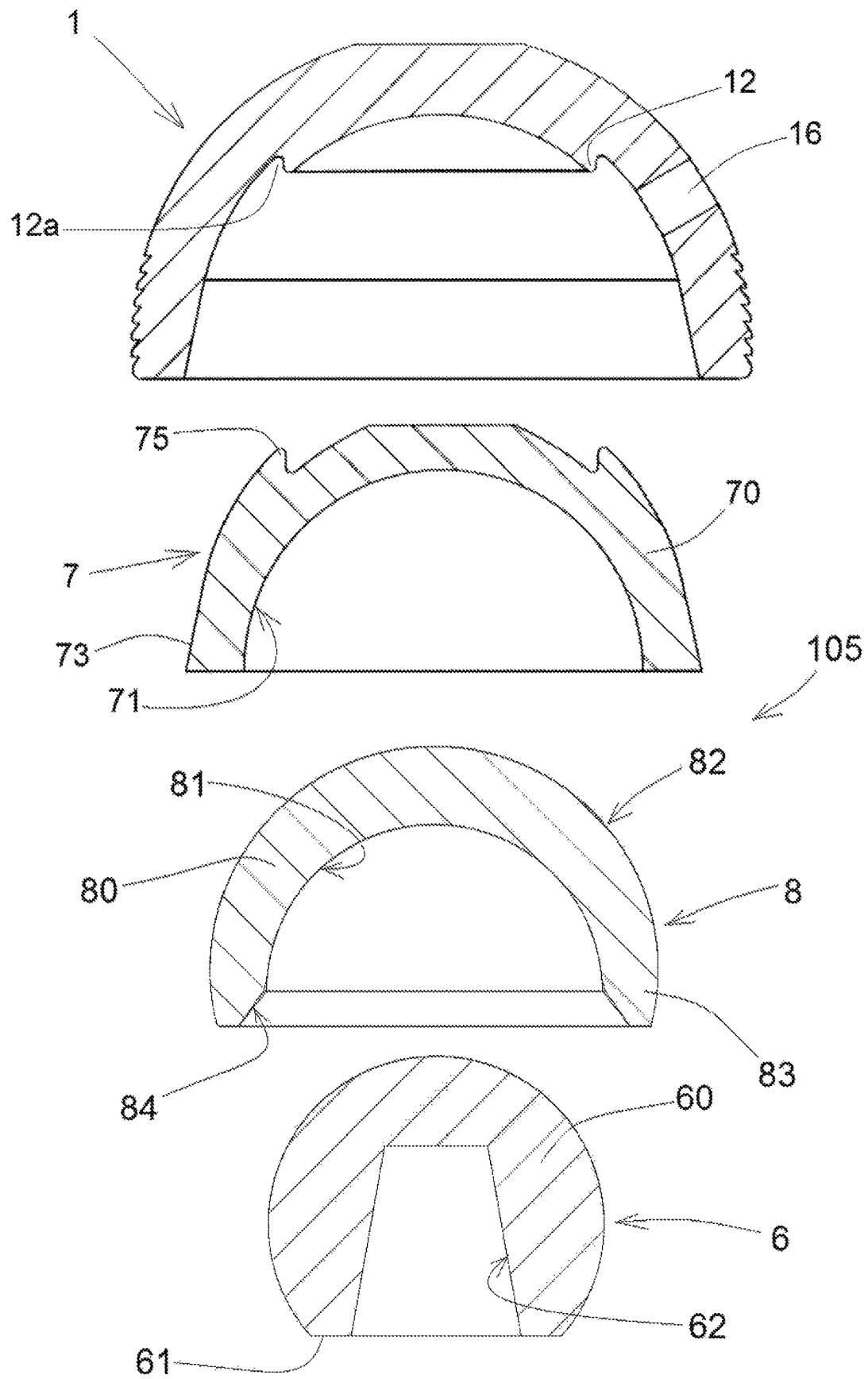
FIG. 9 is an exploded axial view of a second embodiment of a conventional prosthesis with the prosthetic head of FIG. 2.
Figure 10:
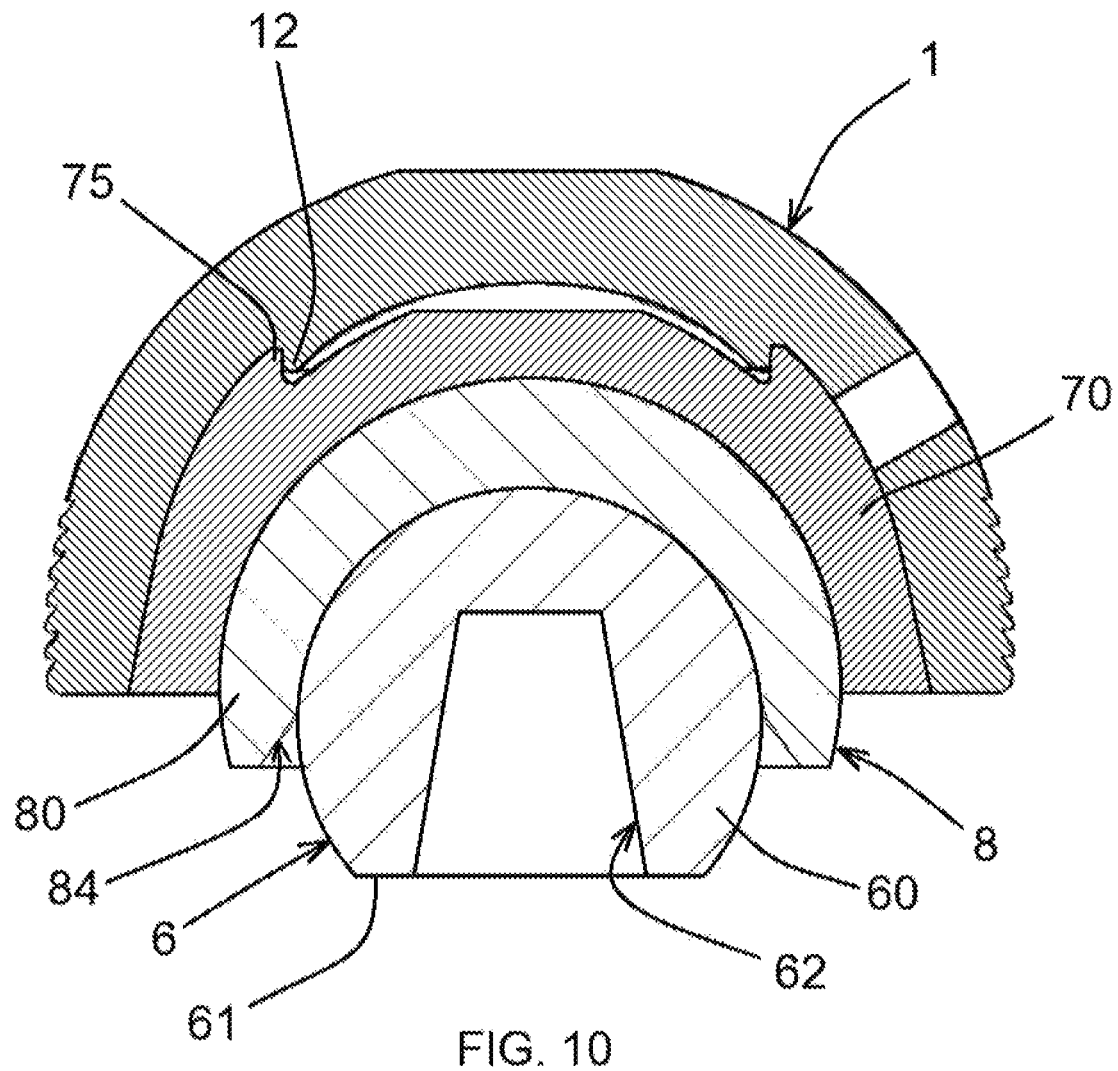
FIG. 10 is an axial view of the conventional prosthesis of FIG. 9 in assembled condition.

With reference to FIGS. 9 and 10, a second embodiment of a conventional prosthesis (105) is described, it being provided with a second insert (8) disposed between the first insert (7) and the ball (6).

The first insert (7) is always coupled with the prosthetic head in conical coupling mode between the truncated-conical portions (73, 17).

The second insert (8) has a body (80) shaped as a hemispherical cup, comprising:
- a hemispherical external surface (82) that is coupled in spherical coupling mode with the internal surface (71) of the first insert; and
- a hemispherical internal surface (81) that is coupled in spherical coupling mode with the body (60) of the ball.

In this way, the prosthesis (105) has a double mobility. A first mobility is obtained between the ball (6) and the second insert (8); a second mobility is obtained between the second insert (8) and the first insert (7).

The external surface (82) of the second insert has the same radius of curvature as the internal surface (71) of the first insert. However, the external surface (82) of the second insert is subtended by a central angle that is higher than the internal surface (71) of the first insert. Therefore, the second insert (8) has an ending portion (83) that abuts in lower position with respect to the lower edge (79) of the first insert. The ending portion (83) of the second insert has a tapered internal surface (84). The purpose of the ending portion (83) of the second insert is to avoid the displacement of the ball (6).

In particular, the ball (60) is inserted by pressure in the second insert (8), in such a way not to come out of the second insert (8) and to rotate freely with respect to the second insert (8).

A Morse cone (not shown) is inserted in the conical housing (62) of the ball and joined to a stem intended to be fixed to the femur. The Morse cone abuts in lower position from the lower edge (61) of the ball. During the movement of the conventional prosthesis (105), the projecting part of the Morse cone is stopped against the tapered surface (84) of the ending portion (83) of the second insert, pushing the second insert (8) and causing a movement of the second insert (8) with respect to the first insert (7).

Figure 11:
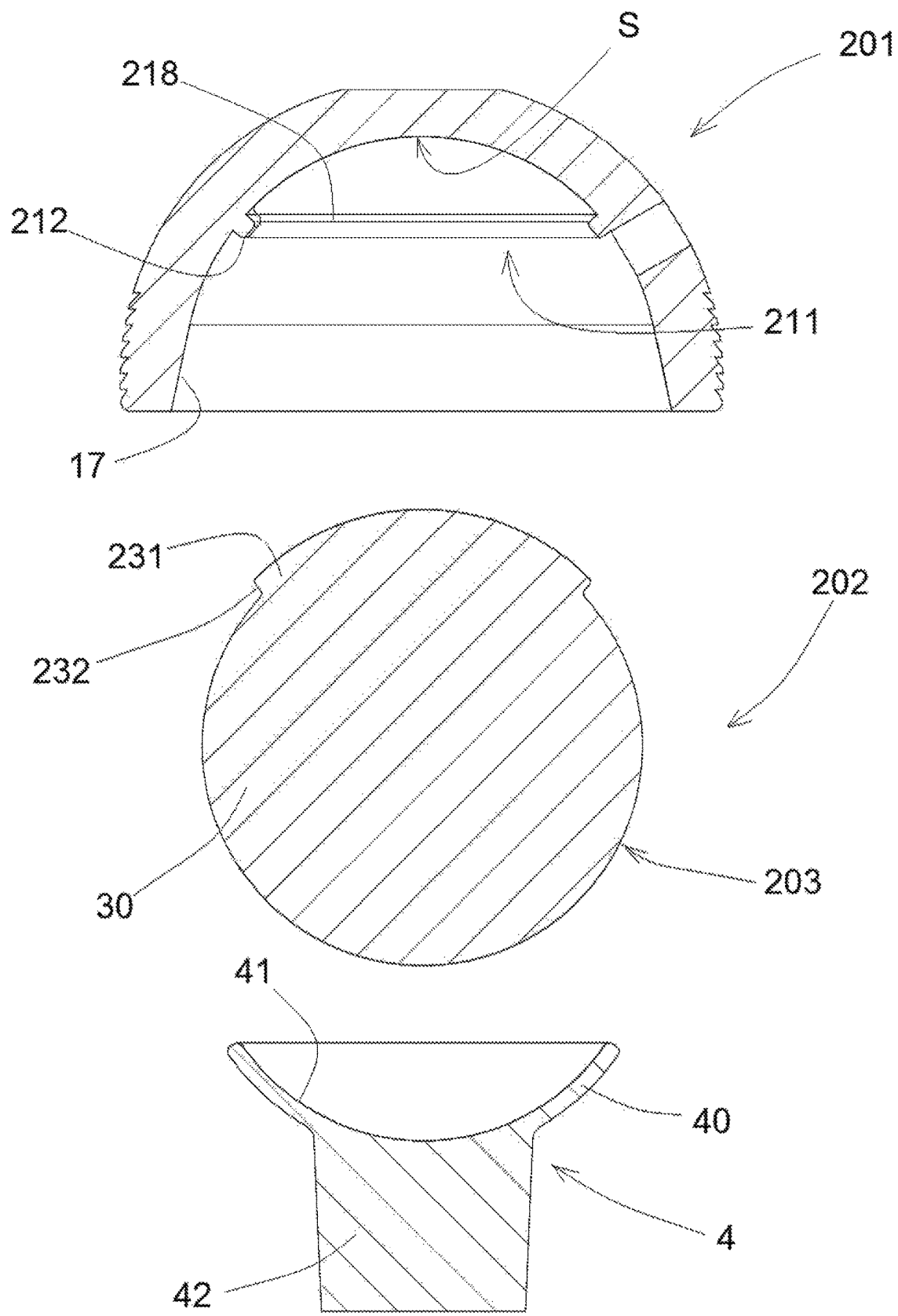
FIG. 11 is an exploded axial view of a second embodiment of the inverse prosthesis according to the invention.
Figure 12:
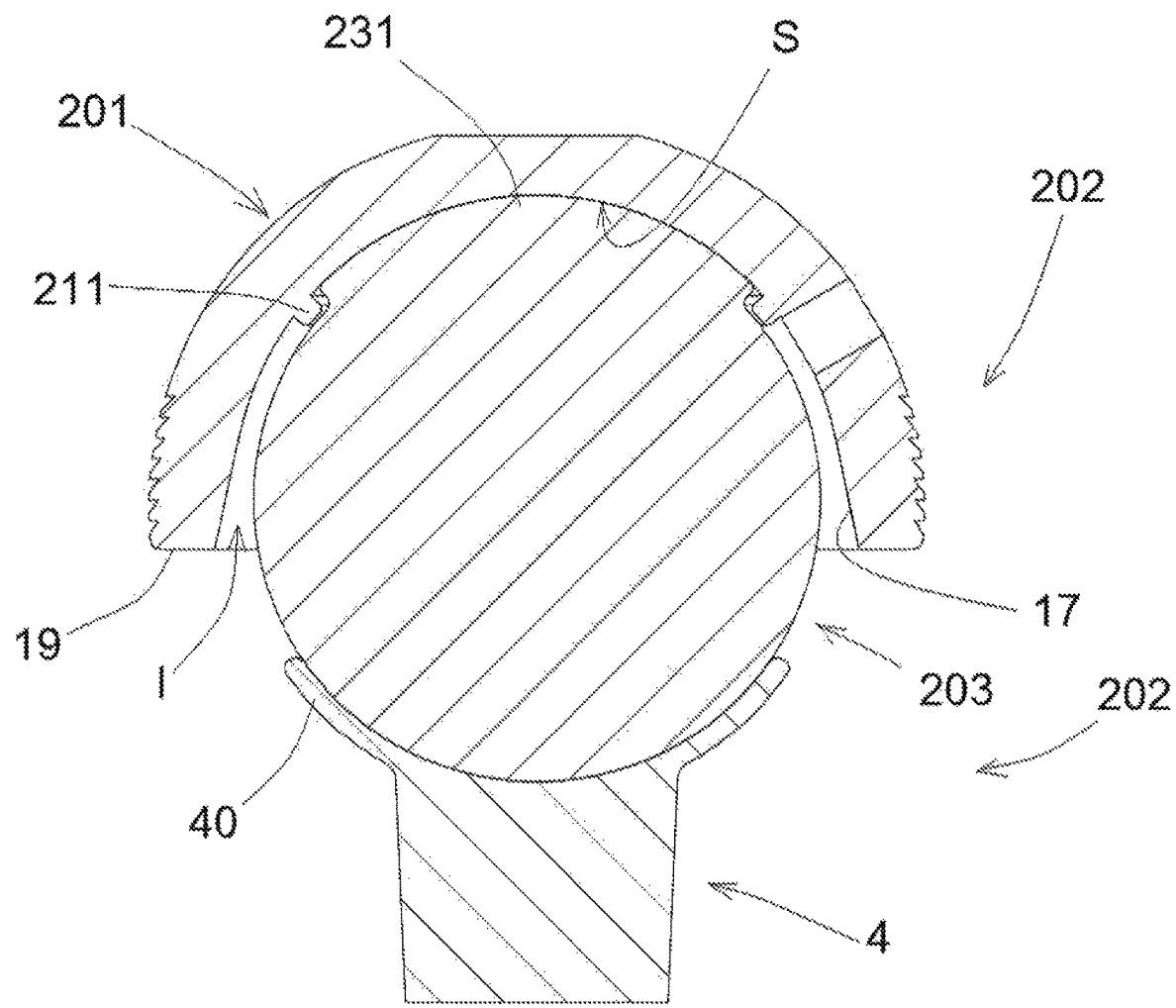
FIG. 12 is an axial view of the inverse prosthesis of FIG. 11 in assembled condition.

With reference to FIGS. 11 and 12 a second embodiment of the inverse hip prosthesis according to the invention is described, which is generally indicated with reference numeral 202.

The inverse prosthesis (202) comprises a prosthetic head (201) with a projection (211) composed of an annular collar that abuts from an internal surface of the prosthetic head in such a way to define a housing (S) shaped as a spherical cap. Such a projection (211) forms an external step (212) and an internal step (218). The prosthetic head (201) always has the truncatedconical portion (17).

The inverse prosthesis (202) has a ball (203) having a spherical body (30) with a projection (231) shaped as a portion of spherical cap that defines an annular step (232) substantially having the same thickness as the step (218) of the projection (211) of the prosthetic head.

The circumference defined by the annular step (232) of the projection of the ball is slightly lower than the circumference defined by the internal annular step (218) of the projection of the prosthetic head. In this way, the projection (231) of the ball (203) is placed into the housing (S) of the prosthetic head. In this way, an air space (I) is formed between the ball (203) of the ball and a peripheral wall of the prosthetic head (201), which is suitable for receiving the body (40) of the distal cup. The movement of the ball (203) with respect to the prosthetic head (201) is constrained by the projection (218) shaped as a collar of the prosthetic head and by the projection (231) shaped as spherical cap of the ball. Otherwise said, the ball (203) can only rotate around an axis passing through the pole of the prosthetic head.

Figure 13:
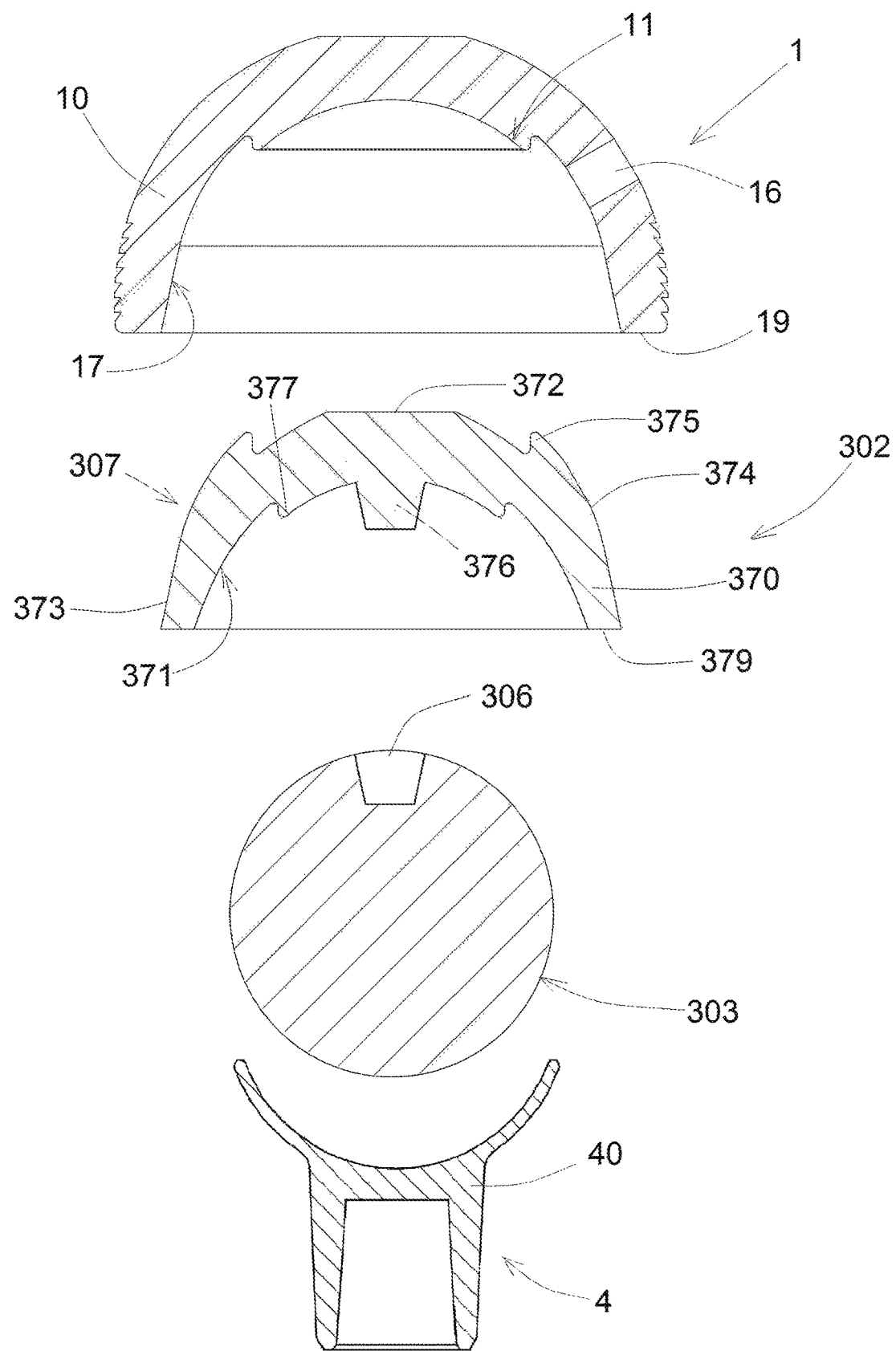
FIG. 13 is an exploded axial view of a third embodiment of the inverse prosthesis according to the invention.
Figure 14:
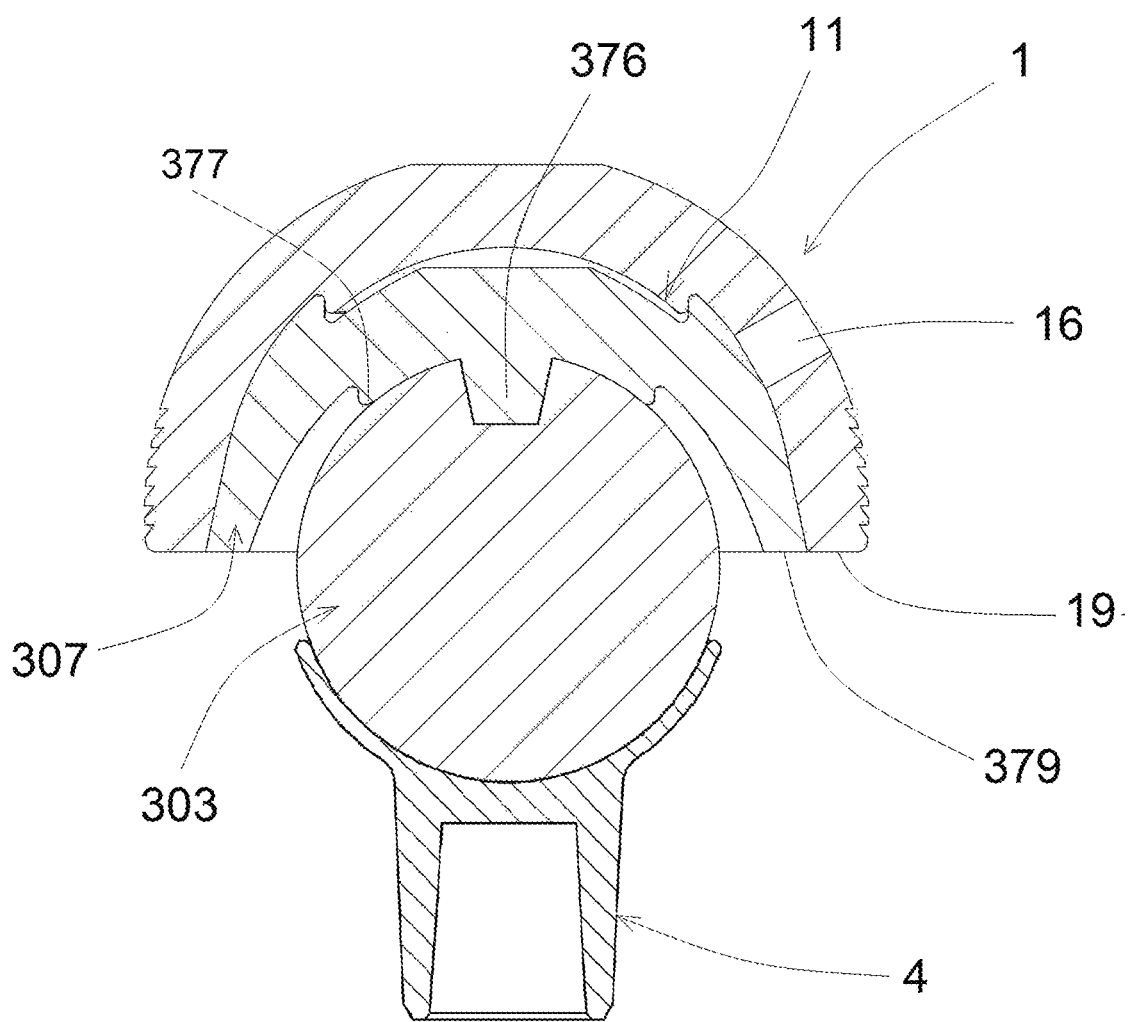
FIG. 14 is a view of the inverse prosthesis of FIG. 13 in assembled condition.

With reference to FIGS. 13 and 14, a third embodiment of the inverse hip prosthesis according to the invention is described, which is generally indicated with reference numeral 302.

The inverse prosthesis (302) comprises the same prosthetic head (1) and the same distal cup (4) as the ones described in the first embodiment of FIGS. 3 and 4.

An insert (307) made of metal comprises a body (370) shaped as a hemispherical cup with a circular lower edge (379).

The body (370) of the insert has an external surface with a flattened pole (372) and a truncated-conical part (373) disposed in peripheral position starting from the lower edge (379). The truncated-conical part (373) of the insert is suitable for being coupled in conical coupling mode with the truncated-conical portion (17) of the prosthetic head.

The external surface of the insert (307) has an intermediate part (374) between the truncated-conical part (373) and the pole (372). An annular collar (375) abuts externally from the intermediate part (374) of the external surface of the insert. In such a way, when the insert (307) is coupled with the prosthetic head (1), the lower edge (19) of the prosthetic head is flush with the lower edge (379) of the insert and the projection (11) of the prosthetic head is disposed inside the collar (375) of the insert and stopped against the intermediate part (374) of the external surface of the body of the insert.

The body (370) has an internal surface (371). An annular step (377) abuts in lower position from the internal surface (371) of the body of the insert. A projection (376) shaped as a Morse cone abuts in lower position from the annular step (377) of the body of the insert in order to be engaged inside a cavity (306) shaped as a traditional Morse cone and obtained in a ball (303) intended to be received in the distal cup (4) in spherical coupling mode.

Alternatively, said ball (303) can be made in one piece with the insert (307).

Numerous variations and modifications can be made to the present embodiments of the invention, which are within the reach of an expert of the field, falling in any case within the scope of the invention.

I claim:

1. A prosthetic head for fixing to a cotyle of a hip prosthesis, the prosthetic head comprising:
- a body having a concave shape, said body having an external surface and an internal surface and a lower edge, the lower edge defining a circumference of said body;
- a plurality of through holes formed in said body;
- a plurality of screws extending respectively through at least some of said plurality of through holes, said plurality of screws adapted to be screwed into the cotyle;
- a projection extending from the internal surface of said body so as to define an annular;
- a truncated-conical portion formed in the internal surface of said body and extending from the lower edge of said body, said truncated-conical portion adapted to couple with a truncated-conical portion of an insert received in said body;
- an insert having an external surface and an internal surface, said insert having a truncated-conical part coupled with the truncated-conical portion of said body, said insert having an annular step extending from the internal surface of said insert and having a projection of a Morse cone shape extending from the annular step;

a ball having a cavity of a Morse cone shape, the cavity housing the projection of said insert; and a distal cup adapted to be fixed to a stem that is to be attached to a femur, said distal cup having a concave cap shape, said distal cup receiving said ball therein.

2. The prosthetic head of claim 1, wherein said truncated-conical portion extends from the lower edge of said body at an angle of between 20° and 30°.

3. The prosthetic head of claim 1, wherein said truncated-conical portion has a coning angle of between 10° and 30°.

4. The prosthetic head of claim 1, further comprising:
a plurality of grooves formed in a peripheral portion of the external surface of said body, said plurality of grooves defining ribs.

5. The prosthetic head of claim 1, wherein said body is formed of a chrome-cobalt alloy.

6. The prosthetic head of claim 1, wherein said body is formed of a titanium alloy.

7. The prosthetic head of claim 1, wherein said body is formed of an electrowelded trabecular titanium.

8. The prosthetic head of claim 1, wherein said body is formed of a trabecular tantalum.

9. The prosthetic head of claim 1, wherein said body has a hydroxyapatite coating on the external surface thereof.

10. The prosthetic head of claim 1, wherein said body has a porous titanium and hydroxyapatite coating on the external surface thereof.

* * * * *